(12) United States Patent
Chang et al.

(10) Patent No.: US 10,245,330 B2
(45) Date of Patent: Apr. 2, 2019

(54) COMPOSITIONS AND METHODS FOR IMAGING

(71) Applicant: The Regents of the University of California, Oakland, CA (US)

(72) Inventors: Christopher J. Chang, Berkeley, CA (US); Alexander R. Lippert, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/642,111

(22) Filed: Jul. 5, 2017

(65) Prior Publication Data

US 2017/0296681 A1    Oct. 19, 2017

Related U.S. Application Data

(62) Division of application No. 13/816,620, filed as application No. PCT/US2011/048630 on Aug. 22, 2011.

(60) Provisional application No. 61/376,063, filed on Aug. 23, 2010.

(51) Int. Cl.

| | | |
|---|---|---|
| *A61K 51/00* | (2006.01) | |
| *A61M 36/14* | (2006.01) | |
| *A61K 51/04* | (2006.01) | |
| *A61K 49/10* | (2006.01) | |
| *C07B 59/00* | (2006.01) | |
| *C07C 59/84* | (2006.01) | |
| *C07C 59/88* | (2006.01) | |
| *C07C 205/57* | (2006.01) | |
| *C07C 255/57* | (2006.01) | |
| *C07D 213/30* | (2006.01) | |
| *C07C 57/30* | (2006.01) | |
| *G01N 33/84* | (2006.01) | |

(52) U.S. Cl.
CPC ........ *A61K 51/0402* (2013.01); *A61K 49/101* (2013.01); *C07B 59/00* (2013.01); *C07C 57/30* (2013.01); *C07C 59/84* (2013.01); *C07C 59/88* (2013.01); *C07C 205/57* (2013.01); *C07C 255/57* (2013.01); *C07D 213/30* (2013.01); *G01N 33/84* (2013.01); *A61K 2123/00* (2013.01); *C07B 2200/05* (2013.01)

(58) Field of Classification Search
None
See application file for complete search history.

(56) References Cited

U.S. PATENT DOCUMENTS

| | | |
|---|---|---|
| 4,268,687 A | 5/1981 | Tang et al. |
| 5,091,171 A | 2/1992 | Yu et al. |
| 5,180,796 A | 1/1993 | Sutherlin |
| 2010/0226859 A1* | 9/2010 | Brindle ................ A61B 5/055 424/9.3 |
| 2011/0033387 A1* | 2/2011 | Schroeder ............ A61K 49/10 424/9.2 |
| 2011/0195928 A1 | 11/2011 | Leech et al. |

FOREIGN PATENT DOCUMENTS

| | | |
|---|---|---|
| WO | WO 2007/050810 | 3/2007 |
| WO | WO 2010/014893 | 2/2010 |
| WO | WO 2009/152102 | 4/2010 |

OTHER PUBLICATIONS

Salahudeen et al. (J. Clin. Invest. 1991, 88, 1886-1893).*
Siegel et al. (J. Am. Chem. Soc. 1979, 101, 2221-2222).*
Månsson et al. (Proc. Int. Soc. Mag. Reson. Med. 2006, 14, 584).*
Larsen et al. (J. Labelled Compd. 1974, 10, 287-296).*
Rappoport, Z. & Marek, I. The Chemistry of Organocopper Compounds R-Cu. West Sussex, England: John Wiley & Sons 2010.*
Halliwell et al. (FEBS Letters 2000, 486, 10-13).*
Braun, et al.; "Parallel Gas Chromatography-Mass Spectrometry and Gas Proportional Counting"; Analytical Chemistry; vol. 48, No. 14, pp. 2284-2285 (Dec. 1976).
Defoin, et al., "A New Liquid Phase Actinometer: Quantum Yield and Photo-CIDNP Study of Phenylglyoxylic Acid in Aqueous Solution", Journal of Photochemistry (May 1986), 33(2):237-255.
Gross, et al., "Bioluminescence imaging of myeloperoxidase activity in vivo", Nat. Med. (Apr. 2009), 15(4):455-461.
Kielland, et al., "In vivo imaging of reactive oxygen and nitrogen species in inflammation using the luminescent probe L-012", Free Radical Biology & Medicine (Sep. 2009), 47(6):237-255.
Larsen, et al.; "Syntheses of $^{14}$C-Labeled Cinnamic, Mandelic, Phenylacetic, Phenylglyoxylic, and Phenylpyruvic Acids."; Journal of Labelled Compounds; vol. X, No. 2, pp. 287-296 (1974).
Lee, et al., "In vivo imaging of hydrogen peroxide with chemiluminescent nanoparticles", Nat. Mater (Aug. 2007),6:765-769.
Lippert, et al., "A Hydrogen Peroxide-Responsive Hyperpolarized 13C MRI Contrast Agent", J. Am. Chem. Soc. (Mar. 2011), 133(11):3776-3779.
Ropp; "Studies Involving Isotopically Labeled Formic Acid and its Derivatives. V. Studies of the Decarbonylation of Formic, Benzoylformic and Triphenylacetic Acids in Sulfuric Acid"; J. Am. Chem. Soc.; vol. 82, No. 4, pp. 842-852 (1960).

\* cited by examiner

*Primary Examiner* — Frederick F Krass
*Assistant Examiner* — Melissa J Perreira
(74) *Attorney, Agent, or Firm* — Boicevic Field & Francis, LLP; Paula A. Borden

(57) ABSTRACT

The present disclosure provides compositions for in vivo imaging of hydrogen peroxide; and methods for detecting hydrogen peroxide in vivo. The compositions and methods find use in various diagnostic applications, which are also provided.

20 Claims, 4 Drawing Sheets

COMPOSITIONS AND METHODS FOR IMAGING

CROSS-REFERENCE

This application is a divisional of U.S. patent application Ser. No. 13/816,620, filed Apr. 10, 2013, which is a national stage application under 35 U.S.C. § 371 of PCT/US11/48630, filed Aug. 22, 2011, which claims the benefit of U.S. Provisional Patent Application No. 61/376,063, filed Aug. 23, 2010, each of which applications is incorporated herein by reference in its entirety.

STATEMENT REGARDING FEDERALLY SPONSORED RESEARCH

This invention was made with government support under Grant No. GM079465 awarded by the National Institutes of Health. The government has certain rights in the invention.

BACKGROUND

Reactive oxygen species (ROS) are involved in various cell signaling pathways that are necessary for cell growth and survival. Correlations have been shown between misregulation of ROS and various diseases, including cancer, diabetes, heart disease, and neurodegenerative diseases. Hydrogen peroxide has been a focus of research geared toward understanding ROS in health and disease because it is a relatively long-lived ROS; thus, it is able to travel through a cell or even across cell membranes before it reacts with a target biomolecule.

Various efforts have been made to detect hydrogen peroxide. For example, fluorescent scaffolds with boronate detection groups have been synthesized for the examination of hydrogen peroxide in cellular systems. Chemiluminescent probes based on peroxalate nanoparticles or on luminol, have been developed.

There remains a need in the field for compounds and methods of detecting ROS, including hydrogen peroxide.

Literature

WO 2007/050810; WO 2009/152102; Lee et al. (2007) *Nat. Mater.* 6765; Gross et al. (2009) *Nat. Med.* 15:455; Kielland et al. (2009) *Free Radical Biol. Med.* 47:760.

SUMMARY OF THE INVENTION

The present disclosure provides compositions for in vivo imaging of hydrogen peroxide; and methods for detecting hydrogen peroxide in vivo. The compositions and methods find use in various diagnostic applications, which are also provided.

DEFINITIONS

Figure 1:
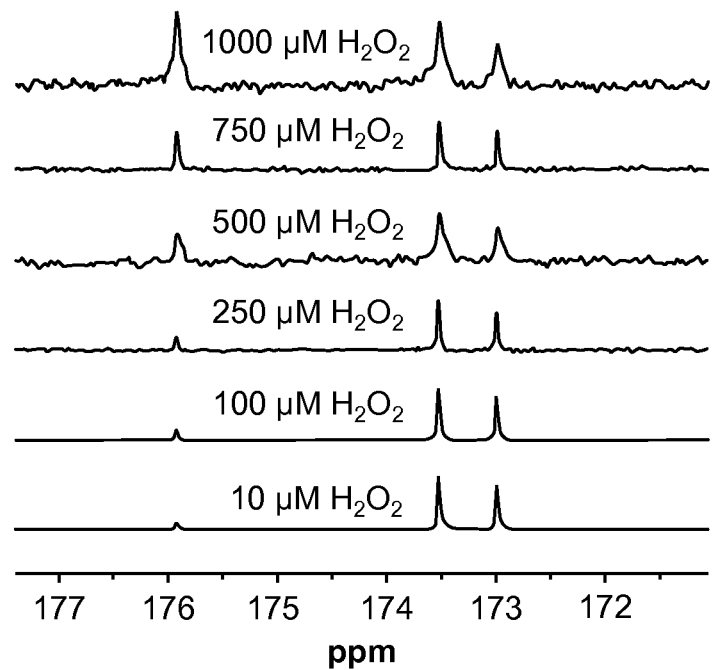
FIG. 1 illustrates the response of hyperpolarized $^{13}$C-benzoylformic acid ($^{13}$C-BFA) to various concentrations of hydrogen peroxide.
Figure 1:
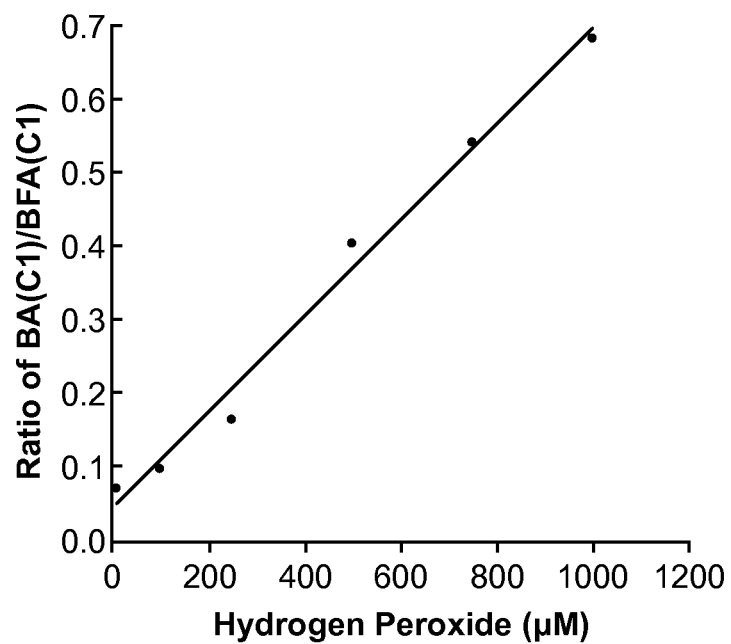

The phrase "in vivo imaging" as used herein refers to methods of detecting the presence of a detectable moiety (e.g., an optically detectable moiety) in a whole, live animal. In vivo imaging may be used to provide two-dimensional as well as three-dimensional (3D) images of an animal. Charge-coupled device cameras, complementary metal oxide semiconductors (CMOS) image sensors, and three-dimensional (3D) tomographers can be used to carry out in vivo imaging.

As used herein, the term "hyperpolarize" or "hyperpolarization" refers to changing the distribution of spins on the available spin states from the Boltzmann distribution. The resulting hyperpolarization is higher than the polarization given by the Boltzmann distribution, which is a function of temperature and magnetic field strength. For example, the term "hyperpolarized" refers to polarized to a level over that found at room temperature and 1 T. These concepts and methods for hyperpolarization are further described in U.S. Pat. Nos. 6,466,814, 7,631,507, and 7,741,844.

The terms "subject," "individual," "host," and "patient" are used interchangeably herein to refer to an animal to which a subject compound is administered. An "individual" includes mammalian and non-mammalian species, including human and non-human animals. Individuals thus include, without limitation, humans, non-human primates, canines, felines, ungulates (e.g., equine, bovine, swine (e.g., pig)), avians, rodents (e.g., rats, mice), and other subjects. Non-human animal models, e.g., non-human mammals, e.g. a non-human primate, a murine (e.g., a mouse, a rat), lagomorpha, etc. may be used for experimental investigations.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes one and more than one such excipient, diluent, carrier, and adjuvant.

As used herein, a "pharmaceutical composition" is meant to encompass a composition suitable for administration to a subject, such as a mammal, e.g., a human. In general a "pharmaceutical composition" is sterile, and is free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intratracheal and the like. In some embodiments the composition is suitable for administration by a transdermal route, using a penetration enhancer other than dimethylsulfoxide (DMSO). In other embodiments, the pharmaceutical compositions are suitable for administration by a route other than transdermal administration. A pharmaceutical composition will in some embodiments include a subject compound and a pharmaceutically acceptable excipient. In some embodiments, a pharmaceutically acceptable excipient is other than DMSO.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and are either pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The term "organic group" and "organic radical" as used herein means any carbon-containing group, including hydrocarbon groups that are classified as an aliphatic group, cyclic group, aromatic group, functionalized derivatives thereof and/or various combinations thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, isopropyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, trifloromethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. Any of the organic groups described herein may be unsubstituted or substituted with one or more substituents. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include chloro and bromo groups.

The term "haloalkyl" refers to an alkyl group as defined above that is substituted by one or more halogen atoms. The halogen atoms may be the same or different. The term "dihaloalkyl " refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl)hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N-($C_1$ to $C_6$ alkyl)carboxamide, protected N-($C_1$ to $C_6$ alkyl)carboxamide, N,N-di($C_1$ to $C_6$ alkyl)carboxamide, trifluoromethyl, N-(($C_1$ to $C_6$ alkyl)sulfonyl)

amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(iso-propyl)phenyl, 2, 3, or 4-ethylphenyl, 2, 3 or 4-(n-propyl)phenyl and the like; a mono or di(alkoxy)phenyl group, for example, 2,6-dimethoxyphenyl, 2, 3 or 4-(iso-propoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy) phenyl group such as 2, 3 or 4-carboxyphenyl or 2,4-di (protected carboxy)phenyl; a mono- or di(hydroxymethyl) phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl) phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl) ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy (n-hexyl), 5-(4'-aminomethylphenyl) -3-(aminomethyl)n-pentyl, 5-phenyl-3-oxo-n-pent-1-yl, (4-hydroxynapth-2-yl) methyl and the like.

As noted above, the term "aromatic" or "aryl" refers to six membered carbocyclic rings.

The term "heteroaroyl" refers to a heteroarylcarbonyl group, i.e., Het-C(=O)—.

The term "aroyl" refers to a arylcarbonyl group, i.e., Ar—C(=O)—.

The term "heteroaryl" refers to an aromatic group of from 1 to 10 carbon atoms and 1 to 4 heteroatoms selected from the group consisting of oxygen, nitrogen, and sulfur within the ring. Such heteroaryl groups can have a single ring (e.g., pyridinyl, imidazolyl or furyl) or multiple condensed rings (e.g., indolizinyl, quinolinyl, benzimidazolyl or benzothienyl), wherein the condensed rings may or may not be aromatic and/or contain a heteroatom, provided that the point of attachment is through an atom of the aromatic heteroaryl group. In certain embodiments, the nitrogen and/ or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, -SO-aryl, -SO-heteroaryl, —SO$_2$-alkyl, —SO$_2$-substituted alkyl, —SO$_2$-aryl, —SO$_2$-heteroaryl, and fused heterocycle.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature, or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Any of the groups described herein may be unsubstituted or substituted with one or more substituents. "Substituted" refers to a group in which one or more hydrogen atoms are independently replaced with the same or different substituent(s). Typical substituents include, but are not limited to, alkylenedioxy (such as methylenedioxy), —M, —$R^{60}$, —$O^-$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2O^-$, —$S(O)_2OH$, —$S(O)_2R^{60}$, —$OS(O)_2O^-$, —$OS(O)_2R^{60}$, $P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$ and —$C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not minor images of one another are termed "diastereomers" and those that are non-superimposable minor images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

A subject compound may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an α-ketoacid compound" includes a plurality of such compounds and reference to "the radioisotope" includes reference to one or more radioisotopes and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compositions for in vivo imaging of hydrogen peroxide; and methods for detecting hydrogen peroxide in vivo. The compositions and methods find use in various diagnostic applications, which are also provided.

A subject compound is substantially non-toxic to a living cell, and thus is suitable for detecting hydrogen peroxide in a living cell in vivo, e.g., in a living cell in an individual, or extracellularly in an individual.

A subject compound can provide for detection of hydrogen peroxide in a living cell in vivo, e.g., in a living cell in an individual, or extracellularly in an individual, where the hydrogen peroxide is present in the living cell in vivo or extracellularly in an individual, at a concentration of from about 100 µM to about 50 µM, from about 50 µM to about 25 µM, from about 25 µM to about 10 µM, from about 10 µM to about 1 µM, from about 1 µM to about 100 nM, from about 100 nM to about 50 nM, from about 50 nM to about 25 nM, from about 25 nM to about 10 nM, or from about 10 nM to about 1 nM. In some embodiments, a subject compound can provide for detection of $H_2O_2$ in a living cell (in vivo), or extracellularly in an individual, in a range of from about 2.5 µM to about 250 µM, in a range of from about 50 µM to about 250 µM, or in a range of from about 2.5 µM to about 1000 µM.

A subject compound provides for selective detection of hydrogen peroxide, compared to other reactive oxygen species (ROS). In some embodiments, a subject compound reacts with hydrogen peroxide, and does not substantially react with ROS other than hydrogen peroxide, e.g., the compound does not substantially react with any of superoxide anion, nitric oxide, peroxyl radical, alkoxyl radical, hydroxyl radical, hypochlorous acid, and singlet oxygen.

Compounds

The present disclosure provides α-ketoacid compounds that react with hydrogen peroxide. A subject α-ketoacid compound can include an acyl group connected to a formic acid group. In certain embodiments, the acyl group is selected from an aroyl or heteroaroyl group. The α-ketoacid compound may include one or more isotopically labeled atoms capable of being hyperpolarized by dynamic nuclear polarization (DNP), for example, a $^{13}C$ or $^{15}N$, isotope label may be included.

In certain embodiments, the α-ketoacid compound is of the structure of Formula (I):

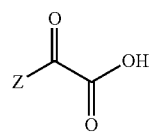

Formula (I)

where Z is a aryl or a heteroaryl group, that includes one or more isotopically labeled atoms capable of being hyperpolarized by DNP. In certain embodiments, in Formula (I), Z is a pyridyl group that may be unsubstituted or substituted with one or more $R^1$ groups, where each $R^1$ is independently selected from hydrogen, deuterium, a halogen, cyano, nitro, a trihalomethyl, an alkoxy, an aryloxy, an alkyl, an aryl, a heterocycle, a thiol, a thioether, an acyl, and hydroxyl. In certain embodiments, in Formula (I), Z is a phenyl group that may be unsubstituted or substituted with one or more $R^1$ groups.

α-Ketoacid compounds of interest include compounds which are capable of reaction with hydrogen peroxide to produce carbon dioxide and a carboxylic acid. Of interest are α-ketoacid compounds that provide selectivity for hydrogen peroxide over other biologically relevant reactive oxygen species (ROS).

In certain embodiments, a substituent may contribute to optical isomerism and/or stereo isomerism of a compound. Salts, solvates, hydrates, and prodrug forms of a compound are also of interest. All such forms are embraced by the present invention. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative. The following are non-limiting examples of subject compounds.

Benzoyl Formic Acids

In certain embodiments, the α-ketoacid compounds are benzoyl formic acids, e.g., α-ketoacid compounds that include a phenyl ring bound to the keto group. The phenyl ring may be substituted or unsubstituted. Substituent bonds to the benzoyl formic acid may be to any available carbon of the phenyl ring. In certain embodiments, the benzoyl formic acid is isotopically labeled with a $^{13}C$ at the keto carbon and/or at any carbon of the phenyl ring.

One embodiment provides a use of a compound having the following structure:

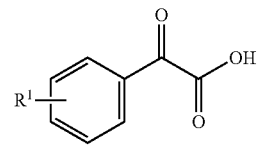

Formula (II)

where $R^1$ is one or more groups, each $R^1$ independently selected from hydrogen, deuterium, a halogen, cyano, nitro, a trihalomethyl, an alkoxy, an aryloxy, an alkyl, an aryl, a heterocycle, a thiol, a thioether, an acyl, and hydroxyl;

where at least one atom is labeled with an isotope suitable for hyperpolarization by DNP. In certain embodiments, the at least one isotopically labeled atom is selected from $^{13}C$ and $^{15}N$.

In certain embodiments, in formula (II), the compound includes a $^{13}C$ labeled atom as shown in one of the following structures:

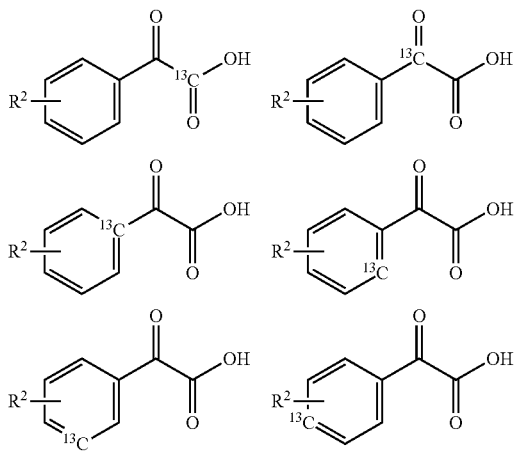

where $R^2$ is one or more groups, each $R^2$ independently selected from hydrogen, deuterium, a halogen, cyano, nitro, a trihalomethyl, and an alkoxy.

In certain embodiments, the compound includes two or more $^{13}C$ labeled atoms. For example, the compound includes two $^{13}C$ labeled atoms as shown in one of the following structures:

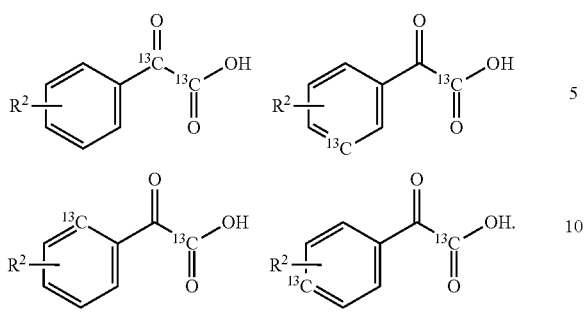

In certain embodiments, the compound includes two or more isotopically labeled atoms at any two or more suitable positions of the compound.

In certain embodiments, a subject compound is of the structure of Formula (III):

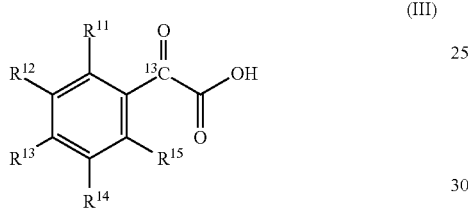

where $R^{11}$, $R^{12}$, $R^{13}$, $R^{14}$ and $R^{15}$ are independently selected from hydrogen, deuterium, a halogen, cyano, nitro, a trihalomethyl, an alkoxy, an aryloxy, an alkyl, an aryl, a heterocycle, a thiol, a thioether, an acyl, and hydroxyl. In particular embodiments, the compound is of the structure of formula (III) except that the $^{13}$C isotopically labeled atom is not positioned at the keto carbon, but at different position.

In certain embodiments, a subject compound is of the structure of one of Formulas (IV)-(IX):

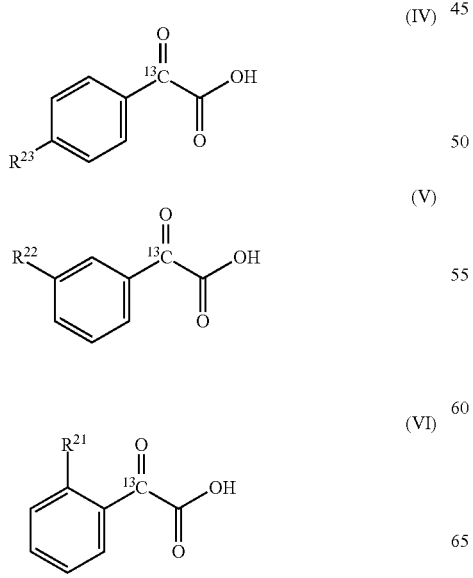

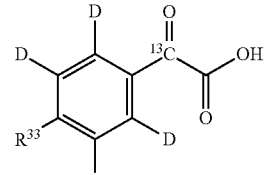

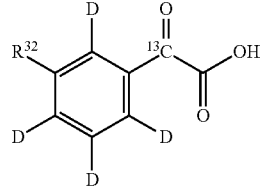

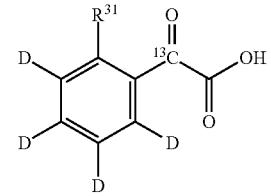

where $R^{21}$, $R^{22}$, $R^{23}$, $R^{31}$, $R^{32}$ and $R^{33}$ are independently selected from hydrogen, deuterium, a halogen, cyano, nitro, a trihalomethyl, an alkoxy, an aryloxy, an alkyl, an aryl, a heterocycle, a thiol, a thioether, an acyl, and hydroxyl.

In particular embodiments, a subject compound has one of the following structures:

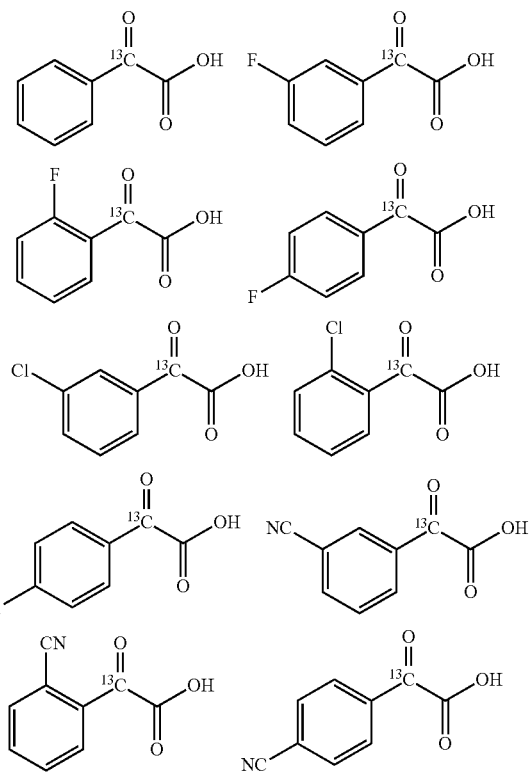

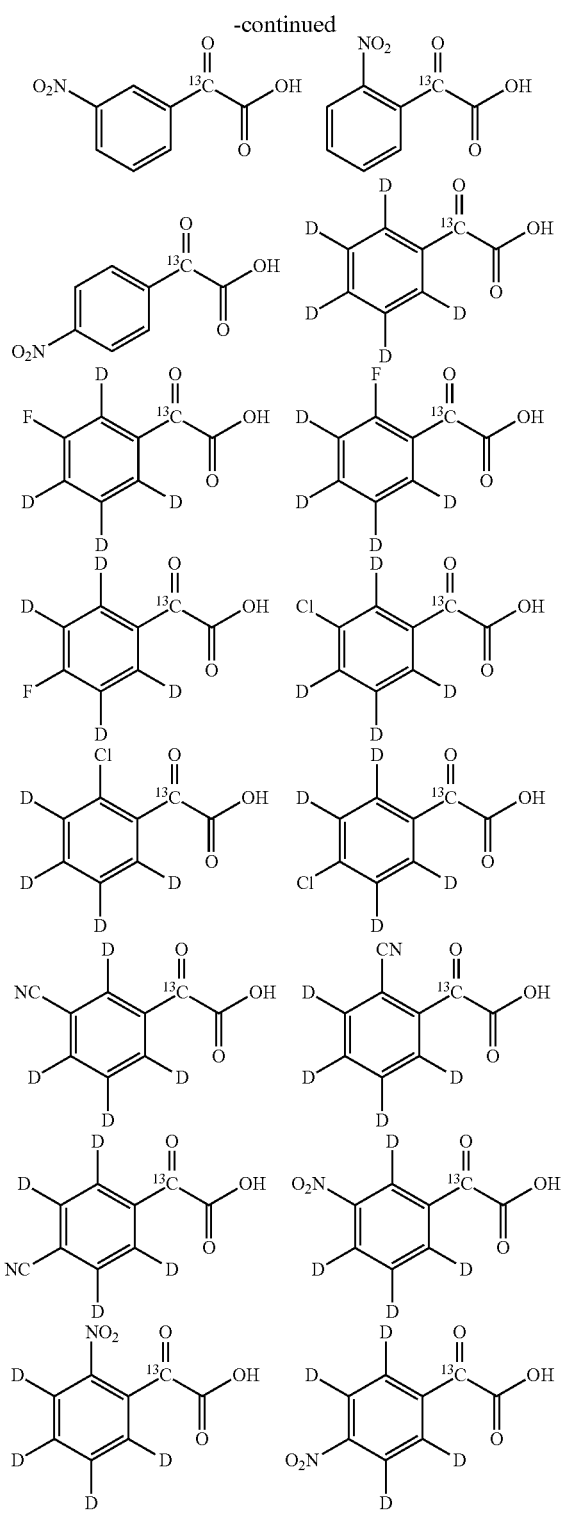

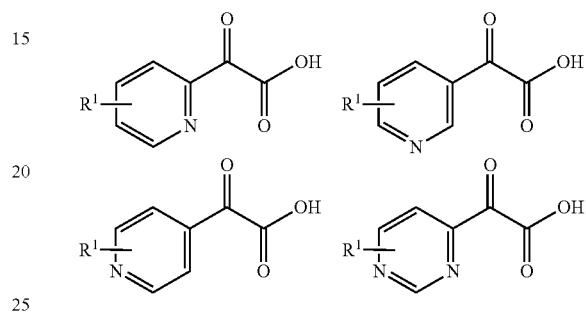

eroaroyl formic acid may be isotopically labeled with a $^{13}C$ atom at the keto carbon, at the formic acid carbon, at any carbon of the heteroaryl ring, or combinations thereof. In certain embodiments, in formula (I), Z is a pyridyl or a pyrimidyl ring, that may be unsubstituted or substituted with one or more $R^1$ groups, where each $R^1$ is independently selected from hydrogen, deuterium, a halogen, cyano, nitro, a trihalomethyl, an alkoxy, an aryloxy, an alkyl, an aryl, a heterocycle, a thiol, a thioether, an acyl, and hydroxyl.

One embodiment provides a use of a compound having one of the following structures:

where $R^1$ is one or more groups, each $R^1$ independently selected from hydrogen, deuterium, a halogen, cyano, nitro, a trihalomethyl, an alkoxy, an aryloxy, an alkyl, an aryl, a heterocycle, a thiol, a thioether, an acyl, and hydroxyl; where at least one atom is labeled with an isotope suitable for hyperpolarization by DNP. In certain embodiments, the at least one isotopically labeled atom is selected from $^{13}C$ and $^{15}N$.

In certain embodiments, the compound includes a $^{15}N$ labeled atom or a $^{15}N$ and a $^{13}C$ label, e.g., as shown in the following structures:

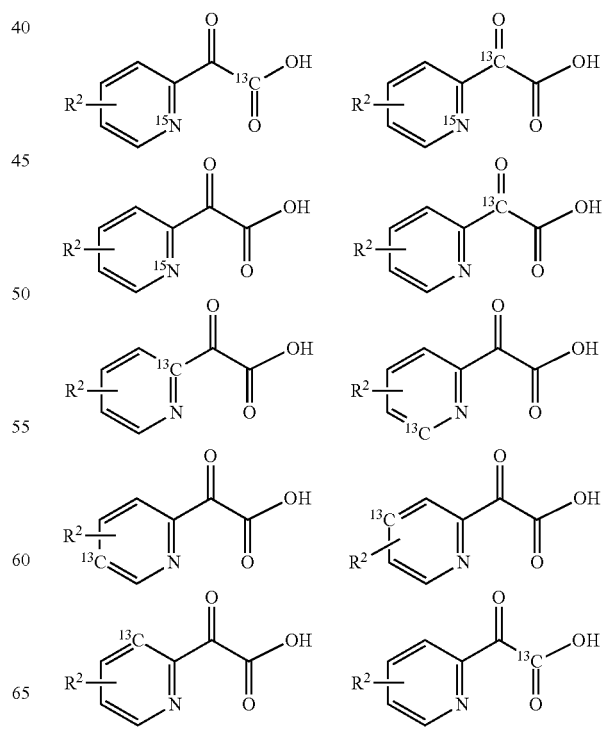

Heteroaroyl Formic Acids

In certain embodiments, the α-ketoacid compounds are heteroaroyl formic acids, e.g., α-ketoacid compounds of the structure of Formula (I) where Z is a heteroaryl ring bound to the keto group. The heteroaryl ring may be substituted or unsubstituted. Substituent bonds to the heteroaroyl formic acid may be to any available carbon of the heteroaryl ring. The heteroaroyl formic acid includes at least one isotopically labeled atom suitable for hyperpolarization. The het-

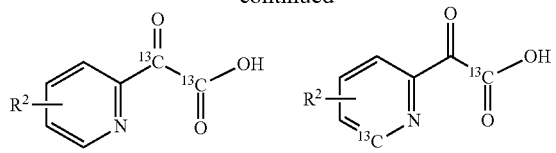

where R[2] is one or more groups, each R[2] independently selected from hydrogen, deuterium, a halogen, cyano, nitro, a trihalomethyl, and an alkoxy.

In certain embodiments, the compound may include two $^{13}$C labeled atoms, or a $^{13}$C and a $^{15}$N labeled atom, or two $^{15}$N labeled atoms. In particular embodiments, the $^{15}$N labeled atoms are quaternary. In particular embodiments, the $^{15}$N atoms do not have any hydrogen substitutents.

In certain embodiments, the compound includes a quaternary $^{15}$N labeled atom, e.g., as shown in the following structures:

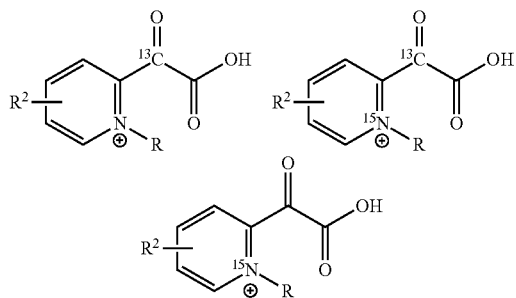

where R[2] is one or more groups, each R[2] independently selected from hydrogen, deuterium, a halogen, cyano, nitro, a trihalomethyl, and an alkoxy; and R is an alkyl group and is not hydrogen.

In certain embodiments, the heteroaroyl formic acid compound includes a pyrimidoyl group. In particular embodiments, the pyrimidoyl formic acid compound includes one or more isotopically labeled atoms independently selected from $^{13}$C and $^{15}$N. In particular embodiments, the pyrimidoyl formic acid compound is substituted with one or more substituents as described above for the pyridinoyl formic acid compounds.

Also provided are pharmaceutically acceptable salts of any of the foregoing compounds.

Compositions

The present disclosure provides compositions, including pharmaceutical compositions, comprising a subject compound. Compositions comprising a subject compound can include one or more of: a salt, e.g., NaCl, MgCl$_2$, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a membrane penetration facilitator; and the like.

The present disclosure provides pharmaceutical compositions comprising a subject compound. A subject compound can be formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

A subject compound can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985.

For oral preparations, a subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycol monomethyl ethers, which melt at body temperature, yet are solidified at room temperature.

Imaging Methods

The present disclosure provides methods for in vivo detection of hydrogen peroxide, and methods for in vivo imaging of cells, tissues, and organs having elevated concentrations of hydrogen peroxide. The methods generally involve administering a subject compound to an individual; and performing an imaging method on the individual, where the imaging method detects the subject compound. As an example, hyperpolarized magnetic resonance imaging is performed. A subject compound is hyperpolarized, e.g., by dynamic nuclear polarization (DNP). The very low natural abundance of $^{13}C$, combined with the pronounced signal enhancement provided by DNP, provides images with very low background signal and a correspondingly high contrast.

A subject method can provide for detection of hydrogen peroxide in a living cell in vivo, e.g., in a living cell in an individual, or extracellularly in an individual, where the hydrogen peroxide is present in the living cell in vivo or extracellularly in an individual, at a concentration of from about 100 µM to about 50 µM, from about 50 µM to about 25 µM, from about 25 µM to about 10 µM, from about 10 µM to about 1 µM, from about 1 µM to about 100 nM, from about 100 nM to about 50 nM, from about 50 nM to about 25 nM, from about 25 nM to about 10 nM, or from about 10 nM to about 1 nM. In some embodiments, a subject compound can provide for detection of $H_2O_2$ in a living cell (in vivo), or extracellularly in an individual, in a range of from about 2.5 µM to about 250 µM, in a range of from about 50 µM to about 250 µM, or in a range of from about 2.5 µM to about 1000 µM.

A subject method can provide for detection of hydrogen peroxide that is at a level that is above a normal control level, e.g., a level that is found normally in an undiseased cell, tissue, or organ. For example, a subject method can provide for detection of hydrogen peroxide that is 10%, 15%, 20%, 25%, 50%, 75%, 2-fold, 3-fold, 5-fold, 10-fold, or more than 10-fold, higher than a normal control level.

Methods for hyperpolarization of a compound are known in the art, and any known method can be used. See, e.g., U.S. Pat. Nos. 7,631,507 and 7,741,844. A subject compound can also be hyperpolarized using a method as described in the Examples. For example, a subject compound in aqueous solution with 15 mM OXO63 radical can be polarized by DNP by irradiating at 90940 MHz.

OXO63 has the structure:

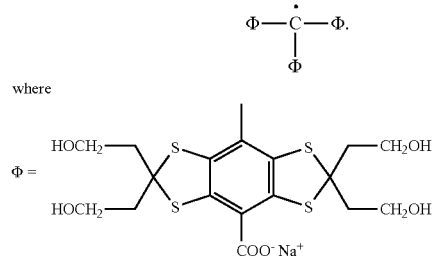

where

Other triarylmethyl-type compounds can be used. See, e.g., Golman et al. (2000) *J. Magn. Reson. Imaging* 12:929; and Ardenkjaer-Larsen et al. (1998) *J. Magn. Reson.* 133:1.

The present disclosure provides a method of detecting hydrogen peroxide in a living cell, tissue, or organ in vivo, e.g., in a living individual. In some embodiments, the method involves administering a subject compound (or a composition comprising a subject compound) to an individual (e.g., a mammal); and detecting a signal generated by reaction of the compound with hydrogen peroxide in a cell, tissue, or organ of the individual. A subject detection method can also be carried out ex vivo, e.g., where a tissue or cells are taken from an individual and imaged.

The present disclosure also provides a method of detecting hydrogen peroxide in an individual, where the hydrogen peroxide is present extracellularly in the individual. In some embodiments, the method involves administering a subject compound (or a composition comprising a subject compound) to an individual; and detecting a signal generated by reaction of the compound with hydrogen peroxide in the individual, where the hydrogen peroxide is present extracellularly in the individual. The hydrogen peroxide can be present in an extracellular fluid (e.g., cerebrospinal fluid, lymph, plasma, and the like) or other extracellular environment.

Suitable methods of detecting a signal generated by reaction of a subject compound with hydrogen peroxide include magnetic resonance imaging (MRI), e.g., hyperpolarized MRI.

A subject detection method can be used to detect the level of hydrogen peroxide in a cell, tissue, or organ in response to an internal or an external stimulus applied to a cell, tissue, organ, or individual. External and internal signals (stimuli) include, but are not limited to, infection of a cell, tissue, or organ by a microorganism, including, but not limited to, a bacterium (e.g., *Mycobacterium* spp., *Shigella*, *Chlamydia*, and the like), a protozoan (e.g., *Trypanosoma* spp., *Plasmodium* spp., *Toxoplasma* spp., and the like), a fungus, a yeast (e.g., *Candida* spp.), or a virus (including viruses that infect mammalian cells, such as human immunodeficiency virus, foot and mouth disease virus, Epstein-Barr virus, and the like; viruses that infect plant cells; etc.); excessive heat relative to the normal range for the cell, tissue, or organ; excessive cold relative to the normal range for the cell, tissue, or organ; an effector molecule such as a hormone, a cytokine, a chemokine, a neurotransmitter; an ingested or applied drug; a ligand for a cell-surface receptor; a ligand for a receptor that exists internally in a cell, e.g., a nuclear receptor; hypoxia; a change in cyoskeleton structure; light; dark; caloric restriction; caloric intake; mitogens, including, but not limited to, lipopolysaccharide (LPS), pokeweed mitogen; stress; antigens; sleep pattern (e.g., sleep deprivation, alteration in sleep pattern, and the like); an apoptosis-inducing signal; electrical charge (e.g., a voltage signal); extracellular ion concentration or intracellular ion concentration, exemplary ions including sodium ions, potassium ions, chloride ions, calcium ions, and the like; presence or absence of a nutrient; metal ions; a transcription factor; a tumor suppressor; cell-cell contact; adhesion to a surface; peptide aptamers; RNA aptamers; intrabodies; and the like.

A subject detection method can be used to detect the level of hydrogen peroxide in a cell in vivo or in an extracellular fluid or other tissue in vivo as a function of a particular physiological state. For example, the level of hydrogen peroxide is measured in a cell, tissue, or organ in an individual, or in an extracellular fluid in an individual, when the cell, tissue, or organ is in a first physiological state; and the level of the hydrogen peroxide is measured in the same cell, tissue, or organ when the cell, tissue, or organ is in a second physiological state. For example, the first physiological state could be the absence of a disease state or absence of a condition; and the second physiological state could be the presence of the disease state or presence of the condition. Thus, for example, the level of hydrogen peroxide can be measured in cells, a tissue, or an organ of an individual to detect the presence of a disease state or a condition. Disease states and other conditions that are associated with altered hydrogen peroxide levels include, but are not limited to, cancer, inflammation, aging, cardiovascular disease, diabetes, neurodegenerative disease, and stroke.

A subject detection method can be used to detect the level of hydrogen peroxide in a cell, tissue, or organ in an individual over time. For example, the level of hydrogen peroxide is detected in the cell, tissue, or organ at a first time and at a second time; and the levels of hydrogen peroxide detected at the first and second times are compared. In some embodiments, the first time is before treatment with an agent (e.g., a therapeutic agent); and the second time is after treatment with an agent. In these embodiments, the level of hydrogen peroxide can be used to determine the effect of treatment of an individual with the agent. In other embodiments, the first time is at a first age of an individual; and the second time is at a second age of the individual. In these embodiments, the change in level of hydrogen peroxide with age can be monitored. The methods can also be used to monitor the progression of a disease or condition over time.

A subject compound can be used to determine the effect that an agent has on the level of hydrogen peroxide in a cell, tissue, or organ in an individual. Agents that can be tested for an effect on the level of hydrogen peroxide in a cell, tissue, or organ include, but are not limited to, therapeutic agents; growth factors; neurotransmitters; anesthetics; hormones; metal ions; and any other agent that can be administered to an individual.

A subject compound can be administered to an individual via any number of modes and routes of administration. In some embodiments, a subject compound is administered systemically (e.g., via intravenous injection; via oral administration; etc.). In other embodiments, a subject compound is administered locally. A subject compound can be administered intravenously, intratumorally, peritumorally, orally, topically, subcutaneously, via intraocular injection, rectally, vaginally, or any other enteral or parenteral route of administration. In certain cases, a subject compound is administered intravenously.

Individuals who are suitable subjects of a subject detection method include individuals who have or who are suspected to have a disease or disorder characterized at least in part by an excess of hydrogen peroxide. Such diseases and disorders include, but are not limited to, cancer (e.g., prostate cancer), a neurodegenerative disease, diabetes, cardiovascular disease, an inflammatory disease, and stroke.

Individuals who are suitable subjects of a subject detection method include individuals who are undergoing or who have undergone treatment for a disease or disorder characterized at least in part by an excess of hydrogen peroxide.

A subject detection method is suitable for use in diagnosis of a disease or disorder characterized at least in part by an excess of hydrogen peroxide. A subject detection method is suitable for use in monitoring progression of a disease or disorder characterized at least in part by an excess of hydrogen peroxide. A subject detection method is suitable for use in determining efficacy of a therapeutic agent or other treatment for a disease or disorder characterized at least in part by an excess of hydrogen peroxide.

A subject detection method is suitable for use in research applications and drug development applications, e.g., to determine the effect of a therapeutic agent that is under development for treatment of a disease or disorder characterized at least in part by an excess of hydrogen peroxide. For example, an individual (e.g., a non-human mammal such as a rat or a mouse; a human who is taking part in a clinical trial) who has a disease or disorder characterized at least in part by an excess of hydrogen peroxide is subjected to a first imaging method (e.g., MRI); the individual is then administered with a test agent that is being tested for efficacy in treating a disease or disorder characterized at least in part by an excess of hydrogen peroxide; the individual is administered with a subject compound that has been hyperpolarized; and the individual is then subjected to a second imaging method, where the results of the second imaging method are compared to the results of the first imaging method. A reduction in the levels of hydrogen peroxide in a tissue or organ after administration to the individual of the test agent, compared to the levels of hydrogen peroxide in the tissue or organ before administration to the individual of the test agent, indicates that the test agent may be considered a candidate agent for treatment of the disease or disorder.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); ppm, parts per million; and the like.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 1

Response of Hyperpolarized $^{13}$C-BFA to Various Concentrations of hydrogen peroxide $^{13}$C-BFA has suitable properties for polarization by DNP in that it is soluble forming >5 M solutions in water and readily forms a glass upon flash freezing. A 5 M solution of $^{13}$C-BFA in water was prepared with 15 mM OXO63 radical and polarized by DNP by irradiating at 90940 MHz. A buildup time constant of 830 s provided ~5% polarization (5450-fold enhancement factor) after 45 minutes. The spectroscopic detection of $H_2O_2$ of the probe was accomplished by rapidly dissolving polarized samples of $^{13}$C-BFA in 100 mM phosphate buffer at pH 7.8 to a final concentration of 5 mM, followed by reaction with various concentrations of hydrogen peroxide.

FIG. 1a shows the $^{13}$C-NMR spectra of hyperpolarized $^{13}$C-BFA after 21 s of reaction with 10, 100, 250, 500, 750, and 1000 μμM $H_2O_2$ in 100 mM phosphate buffered at pH 7.8 with 0.3 mM EDTA. Single scan spectra were acquired every 3 s with a 5° pulse, except for 10 and 100 μμM which were acquired after 21 s with a 90° pulse. The labeled $^{13}$C peak of the produced benzoic acid was at 176 ppm while the doublet at 173.5 ppm was the unlabeled carboxylate carbon of unreacted $^{13}$C-BFA. FIG. 1b shows a plot of the ratio of integrated peaks of benzoic acid C1 to benzoylformic acid C1 after 21 s of reaction with 10, 100, 250, 500, 750, and 1000 μM $H_2O_2$.

The integrated ratio of the benzoic acid (C1) peak to the unlabeled BFA (C1) peak displayed a maximum after 21 s of reaction and good linear correlation to the concentration of added hydrogen peroxide (FIG. 1b). In order to observe lower hydrogen peroxide concentrations of 10 and 100 μM, a single 90° pulse after 21 s was used to acquire the maximum signal. The attained ratios also fit with the linear correlation, indicating that hyperpolarized $^{13}$C-BFA can detect micromolar concentrations of hydrogen peroxide in vitro.

Example 2

Response of benzoylformic acid to Various Biologically Relevant ROS

Figure 2:
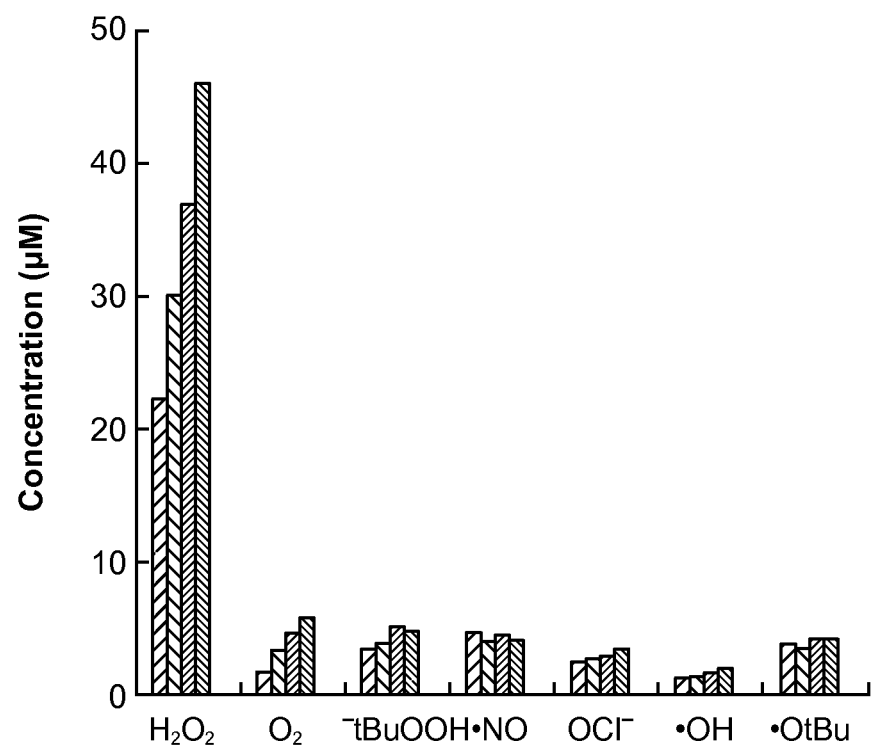
FIG. 2 illustrates the response of 50 µM benzoylformic acid to various biologically relevant ROS. Concentrations of benzoic acid measured over time are shown.

Selectivity assays using high performance liquid chromatography (HPLC) methods were used to demonstrate that compounds of the invention are selective for the detection of $H_2O_2$ by magnetic resonance imaging over other biologically relevant ROS (FIG. 2).

FIG. 2 shows the response of 50 μM benzoylformic acid (BFA) to various ROS in 20 mM HEPES buffered at pH 7.4. All ROS were added at 5 mM, except for $O_2^-$ which was generated enzymatically at a rate of 24 μmol/min for 120 min (2.9 mM total). Concentrations of benzoic acid were measured by HPLC after 0, 5, 10, 15, and 20 min of reaction except for $O_2^-$ which was measured after 0, 30, 60, 90, and 120 min of reaction.

Example 3

Images of the Reaction of $^{13}$C-BFA with $H_2O_2$

Figure 3:
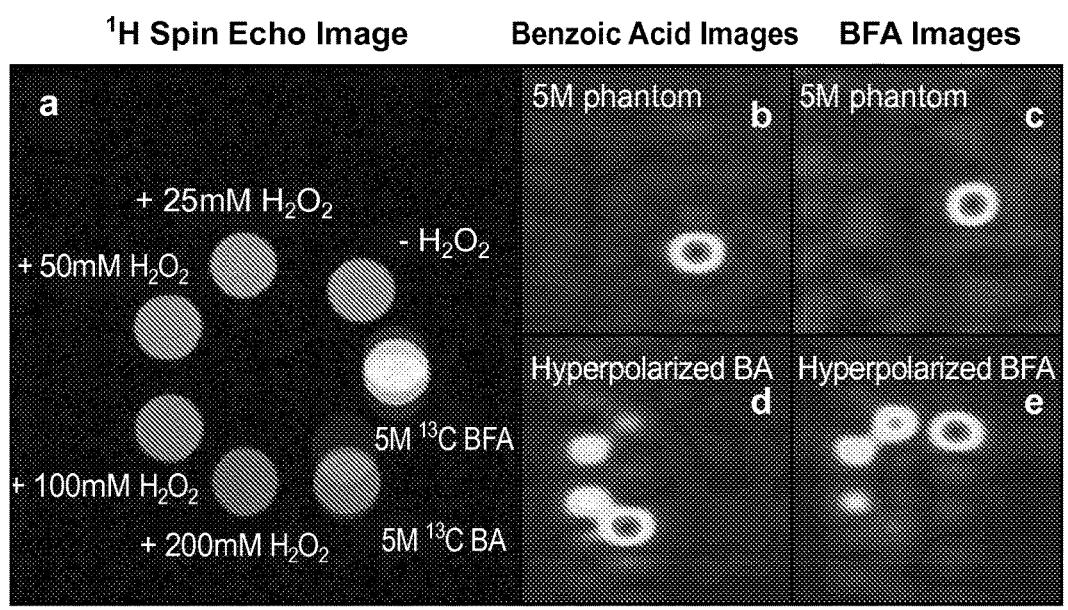
FIG. 3 shows phantom images of hyperpolarized $^{13}$C-BFA and its response to hydrogen peroxide: (a) $^1$H spin echo image; (b) selective excitation of $^{13}$C-BFA; (c) selective excitation of $^{13}$C-benzoic acid ($^{13}$C-BA); (d) selective excitation of $^{13}$C-BFA buffered at pH 7.8; and (e) selective excitation of $^{13}$C-BA buffered at pH 7.8.

Phantom images were attained of the reaction of $^{13}$C-BFA with $H_2O_2$ using a 600 MHz NMR equipped with an imaging coil (FIG. 3). Seven tubes were imaged: 20 mM hyperpolarized $^{13}$C-BFA in 100 mM phosphate, 0.3 mM EDTA buffered at pH 7.8 with 0, 25, 50, 100, and 200 mM $H_2O_2$, thermally polarized 5 M $^{13}$C-benzoic acid in dimethyl acetamide, and thermally polarized $^{13}$C-BFA in $H_2O$. First, $^1$H spin echo images were acquired of all the tubes to indicate tube placement (FIG. 3a). Next, $^{13}$C-MRI images were obtained using frequency specific excitation pulses to obtain images of thermally polarized $^{13}$C-benzoic acid in dimethyl acetamide (FIG. 3b), thermally polarized $^{13}$C-BFA in $H_2O$ (FIG. 3c), hyperpolarized $^{13}$C-benzoic acid in 100 mM phosphate buffer at pH 7.8 (FIG. 3d), and $^{13}$C-BFA in 100 mM phosphate buffer at pH 7.8 (FIG. 3e).

For the thermal samples, an alternative solvent for $^{13}$C-benzoic acid and an unbuffered system for $^{13}$C-BFA were used. This caused a slight 2-3 ppm change in the chemical shifts of these species requiring the corresponding frequency specific pulse for these images.

The thermally polarized 5 M phantoms in FIGS. 3b and 3c are magnified 10× compared to the hyperpolarized 20 mM phantoms in FIGS. 3d and 3e indicating a marked signal enhancement of several orders of magnitude. In FIG. 3d, a clear increase in the intensity of the $^{13}$C-benzoic acid images was observed with increasing $H_2O_2$ concentration. A corresponding decrease in the intensity of the $^{13}$C-BFA images was also observed. These experiments demonstrate that hydrogen peroxide may be imaged with hyperpolarized $^{13}$C-BFA using $^{13}$C-MRI.

Example 4

Rate Constants and Hammett σ-parameters of Compounds

Figure 4:
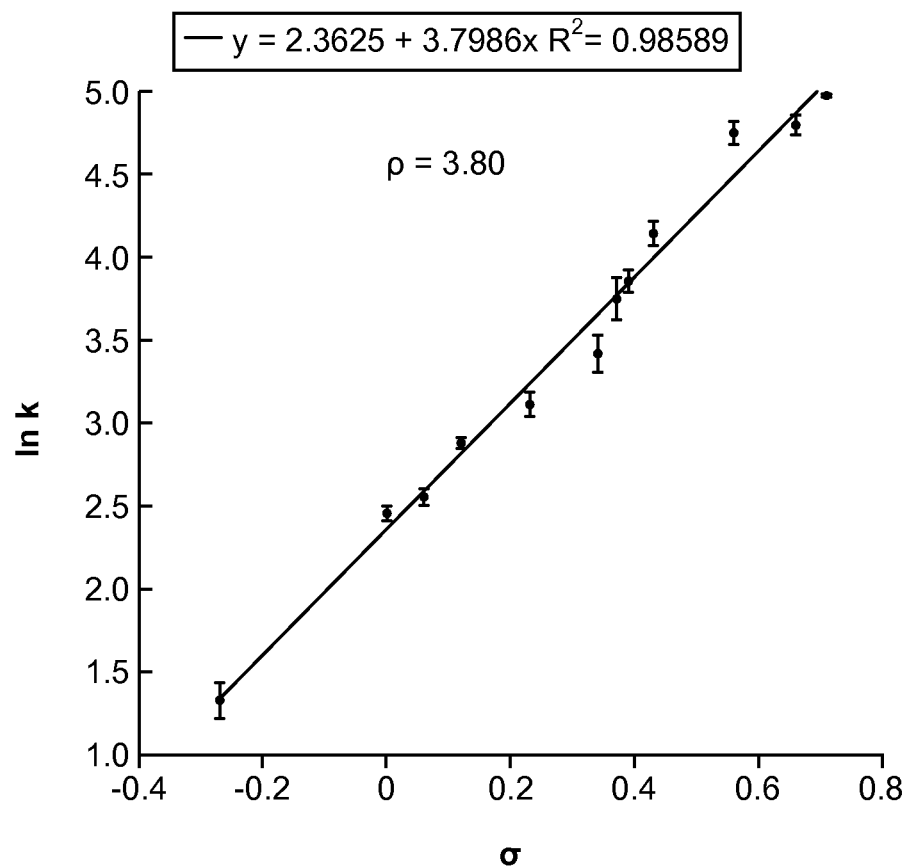
FIG. 4 shows a Hammett plot of the reaction of various α-ketoacid compounds with $H_2O_2$.

A series of compounds were synthesized and kinetically analyzed (Table 1). The measured rate constants correlate well with the Hammett σ parameters giving a ρ value of 3.80 (FIG. 4). Many of the compounds display faster reactivity with $H_2O_2$ than $^{13}$C-BFA.

TABLE 1

Hammett σ parameters and measured rate constants for the reaction of α-ketoacid compounds with $H_2O_2$.

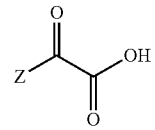

| Entry | R | k (s$^{-1}$ M$^{-1}$) | σ |
|---|---|---|---|
| 1 | 4-MeO | 3.80$^a$ | −0.27 |
| 2 | H | 11.7$^a$ | 0 |
| 3 | 4-F | 12.9$^a$ | 0.06 |
| 4 | 3-MeO | 17.8$^a$ | 0.12 |
| 5 | 4-Cl | 22.6$^a$ | 0.23 |
| 6 | 3-F | 30.7$^a$ | 0.34 |
| 7 | 3-Cl | 42.8$^a$ | 0.37 |
| 8 | 3-Br | 47.4$^b$ | 0.39 |
| 9 | 3-CF$_3$ | 63.1$^b$ | 0.43 |
| 10 | 3-CN | 115.9$^b$ | 0.56 |
| 11 | 4-CN | 121.4$^b$ | 0.66 |
| 12 | 3-NO$_2$ | 144.9$^b$ | 0.71 |

$^a$Second order rate constant measured using 100 μM α-ketoacid and 10 mM $H_2O_2$.
$^b$Second order rate constant measured using 100 μM α-ketoacid and 1 mM $H_2O_2$.

What is claimed is:

1. A method of detecting hydrogen peroxide in a cell, tissue, or organ, or extracellularly in an individual, the method comprising:
   a) administering to the individual a compound of the formula:

wherein Z is heteroaryl group, wherein the substituted aryl or heteroaryl group comprises one or more R$^1$ substituent groups each independently selected from a halogen, cyano, nitro, trihalomethyl, alkoxy, aryloxy, alkyl, aryl, heterocycle, thiol, thioether, acyl and hydroxyl, wherein the compound includes one or more isotopically labeled atoms capable of being hyperpolarized by dynamic nuclear polarization at one or more positions selected from the keto carbon and any atom of the substituted aryl or heteroaryl group; and
   b) detecting a signal produced by the compound upon reaction with hydrogen peroxide, wherein the compound is hyperpolarized and the detecting is by hyperpolarized magnetic resonance imaging.

2. The method of claim 1, wherein hydrogen peroxide is selectively detected in a range of from about 2.5 µM to about 250 µM.

3. The method of claim 1, wherein the individual is a human.

4. The method of claim 1, wherein said detecting is performed at a first time and at a second time that is later than the first time.

5. The method of claim 4, wherein the first time is before administration of a therapeutic agent to the individual, and the second time is after administration of a therapeutic agent to the individual.

6. The method of claim 1, wherein said detecting provides for diagnosis of a disease or disorder characterized at least in part by an excess of hydrogen peroxide.

7. The method of claim 1, wherein said detecting provides for a determination of the efficacy of a therapeutic agent or other treatment for a disease or disorder characterized at least in part by an excess of hydrogen peroxide.

8. The method of claim 7, wherein the disease or disorder characterized at least in part by an excess of hydrogen peroxide is cancer, inflammation, aging, cardiovascular disease, diabetes, neurodegenerative disease, or stroke.

9. The method of claim 1, wherein Z is a substituted pyridyl group.

10. The method of claim 1, wherein Z is a substituted phenyl group.

11. The method of claim 10, wherein the compound comprises at least one $^{13}C$ atom as shown in one of the following structures:

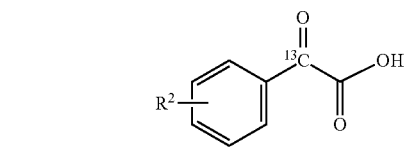

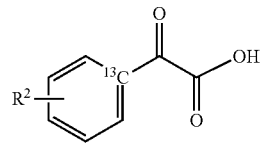 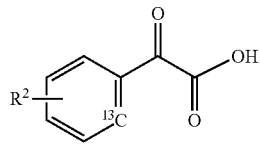

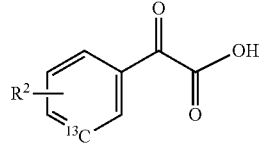 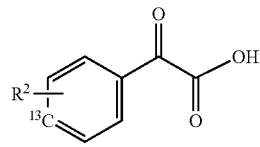

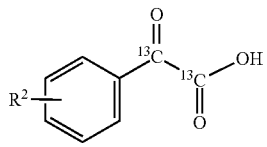 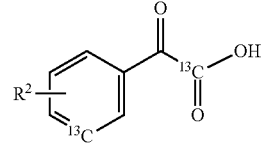

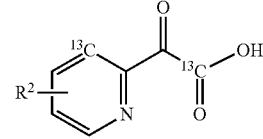

wherein $R^2$ is one or more groups, each $R^2$ independently selected from a halogen, cyano, nitro, a trihalomethyl, an alkoxy, an aryloxy, an alkyl, an aryl, a heterocycle, a thiol, a thioether, an acyl, and hydroxyl.

12. The method of claim 10, wherein the compound is of the formula:

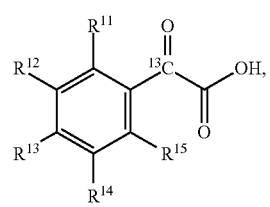

(Formula III)

wherein $R^{11}$, $R^{12}$, $R^{13}$, $R^{14}$, and $R^{15}$ are each independently selected from hydrogen, deuterium, a halogen, cyano, nitro, a trihalomethyl, an alkoxy, an aryloxy, an alkyl, an aryl, a heterocycle, a thiol, a thioether, an acyl, and hydroxyl, wherein at least one of $R^{11}$, $R^{12}$, $R^{13}$, $R^{14}$, and $R^{15}$ is not hydrogen and deuterium.

13. The method of claim 10, wherein the compound is of one of the following formulas:

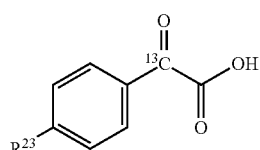

(IV)

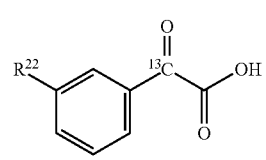

(V)

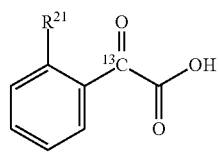

(VI)

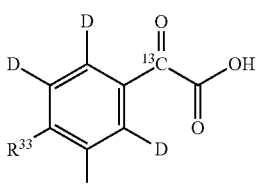

(VII)

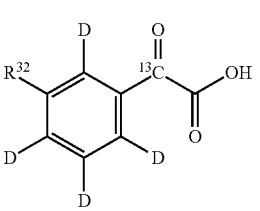

(VIII)

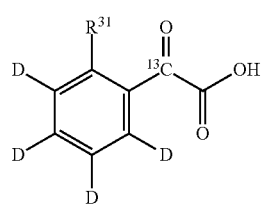

wherein $R^{21}$, $R^{22}$, $R^{23}$, $R^{31}$, $R^{32}$ and $R^{33}$ are each independently selected from halogen, cyano, nitro, trihalomethyl, alkoxy, aryloxy, alkyl, aryl, heterocycle, thiol, thioether, acyl, and hydroxyl.

14. The method of claim 10, wherein the compound is of one of the following structures:

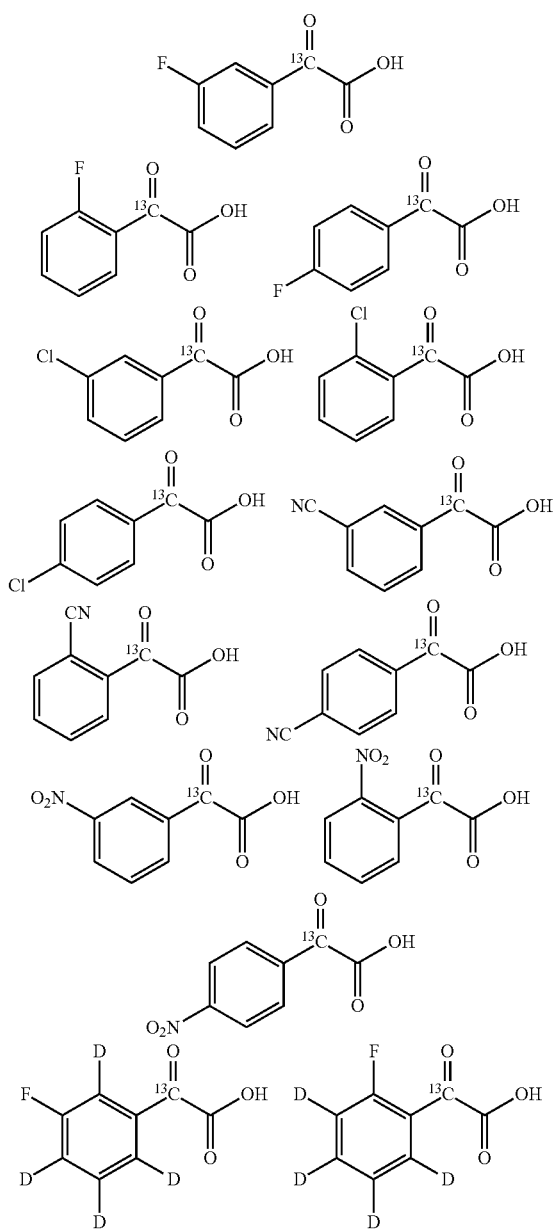

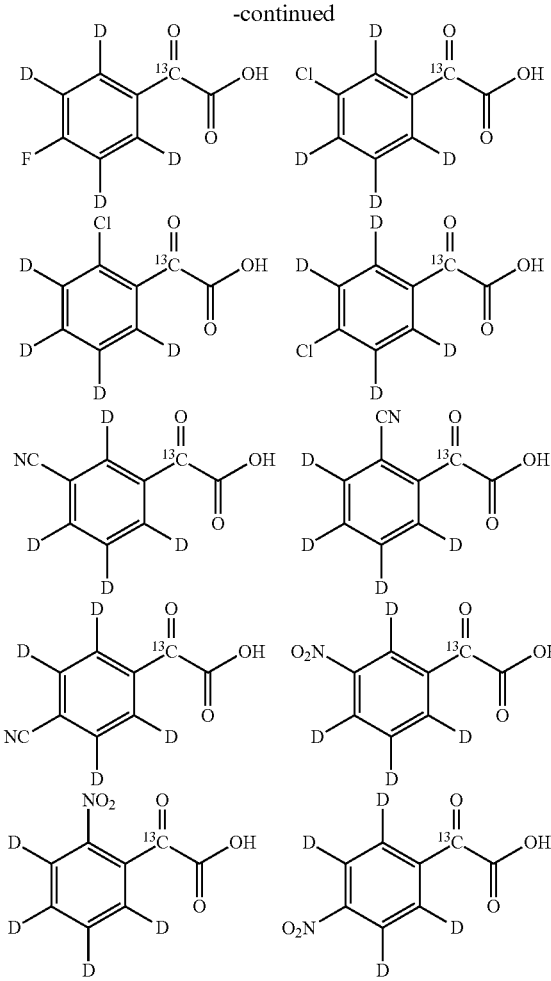

15. The method of claim 9, wherein the compound is of one of the following formulas:

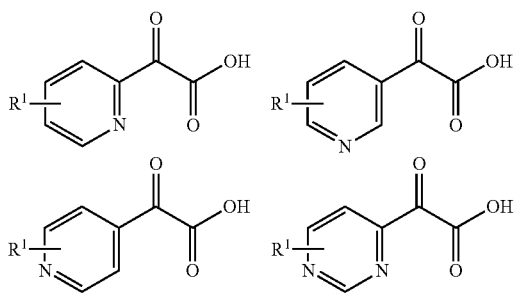

wherein at least one atom selected from the keto carbon and any atom of the pyridyl group is labeled with an isotope suitable for hyperpolarization by DNP.

16. The method of claim 1, wherein the at least one isotopically labeled atom is selected from $^{13}C$ and $^{15}N$.

17. The method of claim 10, wherein the compound comprises two or more $^{13}C$ labeled atoms.

18. A method of detecting hydrogen peroxide in a cell, tissue, or organ, or extracellularly in an individual, the method comprising:
  a) administering to the individual a compound of the formula:

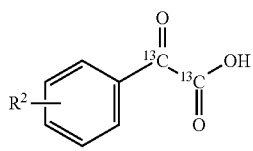

wherein $R^2$ is one or more groups, each $R^2$ independently selected from halogen, cyano, nitro, trihalomethyl, and alkoxy; and b) detecting a signal produced by the compound upon reaction with hydrogen peroxide, wherein the compound is hyperpolarized and the detecting is by hyperpolarized magnetic resonance imaging.

19. The method of claim 18, wherein the compound is selected from one of the following structures:

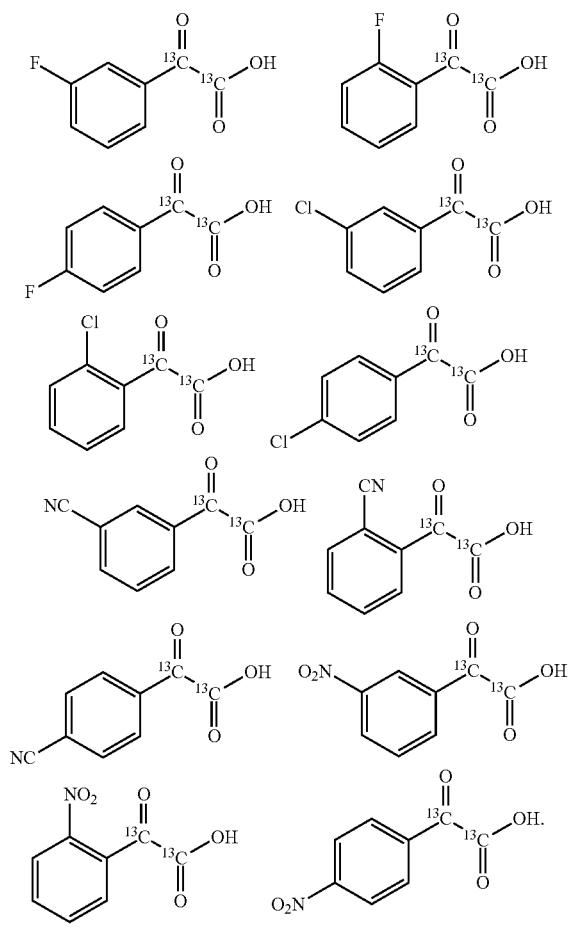

20. A method of detecting hydrogen peroxide in a cell, tissue, or organ, or extracellularly in an individual, the method comprising:

a) administering to the individual a compound of one of the following structures:

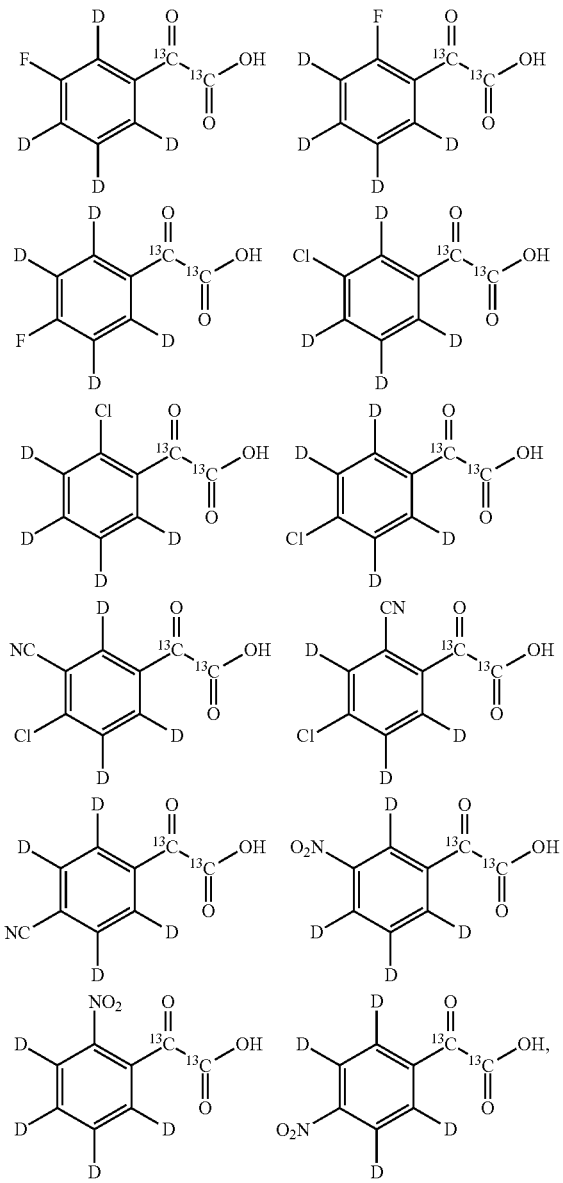

and b) detecting a signal produced by the compound upon reaction with hydrogen peroxide, wherein the compound is hyperpolarized and the detecting is by hyperpolarized magnetic resonance imaging.

* * * * *